US012611407B2

(12) United States Patent
Prathap et al.

(10) Patent No.: US 12,611,407 B2
(45) Date of Patent: Apr. 28, 2026

(54) GASTRO-RESISTANT HIGH-STRENGTH FORMULATION CONTAINING POSACONAZOLE

(71) Applicant: Alfred E. Tiefenbacher (GmbH & Co. KG), Hamburg (DE)

(72) Inventors: Vamshi Ramana Prathap, Telangana (IN); Venkatasimhadri Naidu Kalamata, Hamburg (DE); Ashwini Kumar Mupkalker, Telangana (IN); Srikanth Velchuri, Telangana (IN); Bala Ramesha Chary Rallabandi, Telangana (IN); Kiran Kumar Madallapalli, Telangana (IN); Hendrik Schlehahn, Travenbrueck (DE); Ansgar Fitzner, Hamburg (DE)

(73) Assignee: Alfred E. Tiefenbacher (GmbH & Co. KG), Hamburg (DE)

( * ) Notice: Subject to any disclaimer, the term of this patent is extended or adjusted under 35 U.S.C. 154(b) by 501 days.

(21) Appl. No.: 18/041,449

(22) PCT Filed: Aug. 13, 2021

(86) PCT No.: PCT/EP2021/072649
§ 371 (c)(1),
(2) Date: Feb. 13, 2023

(87) PCT Pub. No.: WO2022/034232
PCT Pub. Date: Feb. 17, 2022

(65) Prior Publication Data
US 2024/0293399 A1 Sep. 5, 2024

(30) Foreign Application Priority Data
Aug. 13, 2020 (IN) .............................. 202011034942

(51) Int. Cl.
*A61K 31/496* (2006.01)
*A61K 9/20* (2006.01)
*A61K 9/28* (2006.01)
*A61K 45/06* (2006.01)

(52) U.S. Cl.
CPC .......... *A61K 31/496* (2013.01); *A61K 9/2018* (2013.01); *A61K 9/2054* (2013.01); *A61K 9/28* (2013.01); *A61K 45/06* (2013.01)

(58) Field of Classification Search
CPC .. A61K 31/496; A61K 9/2018; A61K 9/2054; A61K 9/28; A61K 45/06; A61K 9/145; A61K 9/146
See application file for complete search history.

(56) References Cited

U.S. PATENT DOCUMENTS

| | | | | |
|---|---|---|---|---|
| 10,702,520 | B1 * | 7/2020 | Jain ...................... | A61K 9/2095 |
| 2010/0285122 | A1 * | 11/2010 | Oliyai ..................... | A61P 43/00 |
| | | | | 424/464 |
| 2015/0231081 | A1 | 8/2015 | Kulkarni et al. | |
| 2018/0228798 | A1 * | 8/2018 | Prathap ............... | A61K 9/1617 |
| 2020/0237753 | A1 | 7/2020 | Jain et al. | |

FOREIGN PATENT DOCUMENTS

| | | | |
|---|---|---|---|
| EP | 3006049 | A1 | 4/2016 |
| EP | 3130354 | A1 | 2/2017 |
| EP | 3210599 | A1 | 8/2017 |
| EP | 3342399 | A1 | 7/2018 |
| WO | 1998000113 | A1 | 1/1998 |
| WO | 1999018097 | A1 | 4/1999 |
| WO | 2009129300 | A2 | 10/2009 |
| WO | 2009129301 | A2 | 10/2009 |
| WO | 2009147075 | A2 | 12/2009 |
| WO | 2010000668 | A1 | 1/2010 |
| WO | 2011003992 | A1 | 1/2011 |
| WO | 2011158248 | A2 | 12/2011 |
| WO | 2017025292 | A1 | 2/2017 |
| WO | 2017032908 | A1 | 3/2017 |
| WO | 2019240698 | A2 | 12/2019 |

OTHER PUBLICATIONS

Mudie et al., "Novel High-Drug-Loaded Amorphous Dispersion Tablets of Posaconazole; In Vivo and In Vitro Assessment," Molecular Pharmaceutics, 17(12): 4463-4472 (2020).
International Search Report and Written Opinion issued for PCT/EP2021/072649, dated Dec. 22, 2021 (11 pages).

* cited by examiner

*Primary Examiner* — Jessica Worsham
(74) *Attorney, Agent, or Firm* — Armstrong Teasdale LLP

(57) ABSTRACT
A gastro-resistant high-strength unit dosage form includes a solid solution prepared by hot-melt extrusion, whereby the solid solution contains 300 mg posaconazole and an enteric polymer in a specific weight ratio. The unit dosage form may be a capsule or an optionally film-coated tablet.

14 Claims, No Drawings

GASTRO-RESISTANT HIGH-STRENGTH FORMULATION CONTAINING POSACONAZOLE

CROSS-REFERENCE TO RELATED APPLICATIONS

This application is the § 371 National Stage of International Application No. PCT/EP2021/072649, filed Aug. 13, 2021, which claims priority to Indian application Serial No. 20/201,1034942, filed Aug. 13, 2020, the disclosure of each of which is hereby incorporated herein by reference in its entirety.

The present invention relates to a gastro-resistant high-strength unit dosage form comprising posaconazole.

Posaconazole is a triazole antifungal drug marketed under the tradename Noxafil® as a solution for injection, oral suspension and gastro-resistant tablet for the treatment and prophylaxis of invasive fungal infections. Noxafil® is in particular indicated for the prophylaxis of invasive *Aspergillus* and *Candida* infections in severely immuno-compromised patients, such as hematopoietic stem cell transplant recipients with a graft-versus-host-disease and patients with hematologic malignancies with prolonged neutropenia from chemotherapy. The oral suspension is indicated for the treatment of oropharyngeal candidiasis.

Posaconazole is a white powder with a low aqueous solubility, whereby posaconazole's bioavailability in the oral suspension is significantly enhanced when coadministered with food. For this reason, the oral suspension should be administered during or immediately following a full meal to enhance the oral absorption of the drug. The gastro-resistant tablet has an improved bioavailability and can be administered without regard to food.

It is commonly known that the dissolution behavior of a drug depends on its solid state. Different crystalline forms of a drug usually exhibit different dissolution profiles, whereby amorphous forms are generally much more soluble than their crystalline counterparts. In addition, the chemical and physical stability of a drug are dependent on the solid state. Quite often, metastable crystalline or amorphous forms of a drug have to be stabilized in the pharmaceutical composition in order to prevent chemical degradation and interconversion of the crystalline forms/recrystallization of the amorphous form and, thus, fluctuations in the bioavailability.

WO 99/18097 discloses the crystalline forms I, II and III of posaconazole. Form I is the most stable form that does not convert into any other crystalline form under normal storage conditions or under specific stress conditions. The crystalline forms II and III convert into the form I at temperatures between 100° C. and 125° C.

WO 2009/147075 discloses the crystalline form Y of posaconazole. The form Y is as stable as form I but has a better water solubility, which results in an improved bioavailability.

WO 2010/000668 reports that the crystalline form IV of posaconazole has a better stability in an aqueous suspension and a better water solubility as form I due to a smaller particle size and, thus, larger specific surface area. The crystalline form IV can be directly used for a pharmaceutical composition, i.e. without the need of reducing the particle size by micronization.

WO 2011/158248 discloses the crystalline form V of posaconazole, while WO 2011/003992 discloses the crystalline form II-S from which the other crystalline forms, in particular the crystalline form IV may be obtained.

As an alternative approach for overcoming the solubility problems encountered with posaconazole, WO 98/00113 suggests a pharmaceutical composition comprising a solid solution of the drug within a polymer. The solid solution is prepared by dissolving the drug and a soluble polymer in a suitable organic solvent, followed by removing the solvent, or by dissolving the drug in a suitable organic solvent and adding an insoluble polymer, followed by absorbing the solution into the insoluble polymeric matrix. Preferably, the polymer is povidone or crospovidone.

WO 2009/129301 discloses a solid solution of posaconazole within hydroxypropyl methylcellulose acetate succinate (HPMCAS) by spray-drying a solution containing the drug and the polymer. It is further suggested that the solid solutions may be prepared by using hot-melt extrusion.

WO 2009/129300 discloses the preparation of a solid solution containing posaconazole within a hydroxypropyl methylcellulose derivative, preferably HPMCAS. It has been found that posaconazole forms a solution with the polymer behaving as a eutectic having a melting point below the melting point of the drug (about 169° C.). Hence, the use of hydroxypropyl methylcellulose derivatives for the preparation of the solid solution minimizes thermal decomposition and oxidation of posaconazole during the preparation compared to processes which utilize higher melting polymers. WO 2009/129300 further suggests that the solid solution may additionally contain a plasticizer and an antioxidant.

EP 3 006 049 discloses a solid solution of posaconazole within HPMCAS prepared by hot-melt extrusion. It was found that the use of a specific HPMCAS, which has a hydroxypropyl molar substitution of at least 0.40 and a mole ratio of acetyl to succinyl of less than 1.6 allows the use of lower temperatures in the hot-melt extrusion process.

EP 3 130 354 suggests the use of poly(vinylpyrrolidone/vinylacetate) or a polymer containing ethylene glycol units, e.g. polyvinylcaprolactam/polyvinylacetate/polyethylene glycol graft copolymer, for preparing a solid dispersion containing posaconazole.

US 2015/0231081 suggests a solid solution containing posaconazole dispersed in a polymer other than a hydroxypropyl methylcellulose derivative, such as polyvinyl-pyrrolidone and poly(methacrylic acid/ethyl acrylate).

WO 2017/032908 discloses a solid dispersion of posaconazole within at least two different enteric polymers, whereby the solid dispersion is prepared by wet-granulation. Preferably, the two different enteric polymers are selected from HPMCAS poly(methacrylic acid/methyl methacrylate) and poly(methacrylic acid/ethyl acrylate).

EP 3 342 399 discloses the use of enteric-coated granules containing posaconazole dispersed within a polymer matrix for the preparation of a unit dosage form, preferably a tablet. A suitable matrix polymer is HPMCAS.

WO 2019/240698 discloses the preparation of solid dispersion containing posaconazole, an enteric polymer and a surfactant.

WO 2017/025292 relates to a gastro-resistant pharmaceutical composition comprising posaconazole molecularly dispersed in a mixture containing an enteric polymer and a non-enteric polymer, whereby the mixture is prepared by hot-melt extrusion, and whereby the composition contains an antioxidant.

The recommended dose of NoxafilR is a loading dose of 300 mg twice a day and a maintenance dose of 300 mg once a day. Since the NoxafilR tablet contains 100 mg posaconazole, three tablets have to be given at each time of administration. In order to improve the comfort for the patient when taking posaconazole, a 300 mg posaconazole-containing tablet or capsule formulation was envisaged, so that the patient only needs to take one unit dosage form at each time of administration. However, it was found that simply tripling the amount of drug and pharmaceutical excipients contained in the prior art tablets, as the tablet formulations disclosed in WO 2017/025292, yields in high-strength tablets that are too large to be easily swallowed. However, the obvious measure to reduce the amounts of pharmaceutical excipients in order to prepare a smaller tablet led to enhance precipitation of the drug after dissolution in an aqueous environment. If posaconazole precipitates too quickly after having passed the stomach, its bioavailability is decreased.

The problem underlying the present invention was the provision of a high-strength, gastro-resistant unit dosage form containing posaconazole in a relatively high concentration and that achieves sufficient bioavailability. This problem has been solved by the subject matter as defined in the claims.

The unit dosage form of the present invention is a gastro-resistant pharmaceutical composition. Gastro-resistant formulations are designed to release the drug in the intestines. According to the European Pharmacopoeia 8.0, gastro-resistant dosage forms are delayed-release dosage forms that are intended to resist the gastric fluid and to release their drug(s) in the intestinal fluid. The gastro-resistance minimizes the food effect of the unit dosage form of the present invention and, thus, improves the bioavailability of the drug. The European Pharmacopoeia 8.0 describes, to show gastro-resistance of a tablet, a suitable dissolution test in general chapter '2.9.3. Dissolution test for solid dosage forms'. In this test, the gastro-resistant tablets are exposed for 2 hours to an acid medium (called 'acid stage':typically 0.1 M hydrochloric acid), and afterwards a buffer (typically phosphate buffer) is added and the pH is raised (typically to pH 6.8: called 'buffer stage'). The requirement for a gastro-resistant dosage form is 10% or less dissolution of the drug in the acid stage. Specifically for posaconazole and 100 mg posaconazole delayed release tablets, the U.S. FDA requires in its official dissolution methods database as media 0.01 N HCl in the acid stage and 50 mM phosphate buffer having pH 6.8 in the buffer stage.

The gastro-resistant unit dosage form of the present invention, which is an optionally film-coated tablet or a capsule, comprises 300 mg posaconazole molecularly dispersed in a mixture comprising an enteric polymer and optionally a non-enteric polymer, wherein the mixture is prepared by hot-melt extrusion. It was found that a unit dosage form providing sufficient oral bioavailability and of a size comfortable to the patient may be obtained if the weight ratio of the enteric polymer to posaconazole is in the range of 3.3:1 to 1.5:1, preferably 2.8:1 to 1.8:1: at higher ratios, the unit dosage form may become too large, while at lower ratios, the drug may precipitate after having passed the stomach. The tablet core has a weight of 1200 mg to 1650 mg and the capsule formulation has a weight of 1000 mg to 1100 mg.

The enteric polymer is preferably selected from hypromellose derivatives, cellulose derivatives, polyvinylacetate derivatives and polymethacrylic acid derivatives. Examples of hypromellose derivatives include hydroxypropyl methylcellulose phthalate (hypromellose phthalate, HPMCP, e.g. available as HP-50 or HP-55 from Shin-Etsu Chemical Co., Ltd. Japan), hydroxypropyl methylcellulose succinate and hydroxypropyl methylcellulose acetate succinate (hypromellose acetate succinate, HPMCAS, e.g. available as AQOAT® from Shin-Etsu Chemical Co., Ltd.

Japan). An example of a polyvinylacetate derivative is polyvinylacetate phthalate (PVAP), while examples of cellulose derivatives include cellulose acetate phthalate (CAP), cellulose acetate terephthalate, cellulose acetate isophthalate, cellulose acetate butyrate (CAB), cellulose acetate trimellitate (CAT), methylcellulose acetate phthalate and hydroxypropylcellulose acetate phthalate. Examples of polymethacrylic acid derivatives include poly(methacrylic acid/methyl methacrylate) 1:1 (e.g. available as Eudragit® L 100 from Evonik, Germany), poly(methacrylic acid/methyl methacrylate) 1:2 (e.g. available as Eudragit® S 100 from Evonik, Germany) and poly(methacrylic acid/ethyl acrylate), such as methacrylic acid/ethyl acrylate-copolymer (1:1) Type A (e.g. available as Eudragit® L 100-55 from Evonik, Germany) and the partially-neutralized copolymer methacrylic acid/ethyl acrylate-copolymer (1:1) Type B (e.g. available as Kollicoat® MAE 100P from BASF SE, Germany). According to a preferred embodiment of the present invention, the enteric polymer is HPMCAS and/or a polymethacrylic acid derivative selected from poly(methacrylic acid/methyl methacrylate) and poly(methacrylic acid/ethyl acrylate). In a more preferred embodiment of the present invention, the enteric polymer is a mixture of two enteric polymers, e.g., a mixture of poly(methacry lic acid/ethyl acrylate) and HMPCAS.

The unit dosage form of the present invention may contain a non-enteric polymer that is preferably selected from polyvinylpyrrolidone (povidone), poly(vinyl-pyrrolidone/vinylacetate) (copovidone), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyacry lates, polymethacrylates, vinylacetate polymers such as copolymers of vinyl acetate and crotonic acid, polyvinyl alcohol, partially saponified polyvinylalcohol, macrogolglycerol hydroxystearate, polyethylene glycol, hypromellose, hydroxypropyl cellulose, hydroxyethyl cellulose and maltodextrins.

According to a preferred embodiment of the present invention, the pharmaceutical composition contains an antioxidant. Preferably, the antioxidant is contained in the mixture comprising posaconazole, the enteric polymer and optionally the non-enteric polymer. Examples of antioxidants include butylated hydroxytoluene (BHT), buty lated hydroxyanisole (BHA), sodium or potassium metabisulfite, sodium bisulfite, sodium sulfite, sodium thiosulfate, cysteine, acetyl cysteine, methionine, glutathione, sodium formaldehyde sulfoxylate, ascorbic acid and its derivatives like sodium ascorbate, ascorbyl palmitate, tocopherol and its derivatives, tocopheryl succinate, tocopheryl polyethylene glycol succinate (TPGS), and propyl gallate. Preferably, the antioxidant is propyl gallate. Typically, the antioxidant is present in the composition in an amount of 0.001-2 wt.-%, preferably 0.01-1 wt.-% and most preferred at about 0.2 wt.-%. Optionally the pharmaceutical composition of the present invention contains in addition an antioxidant synergist, e.g. citric acid, tartaric acid, or ethylenediaminetetraacetic acid (EDTA).

The mixture present in the unit dosage form of the present invention may additionally contain a monomeric plasticizer, e.g. triethyl citrate, triacetin, dibutyl sebacate, diethyl phthalate, glycerylmonostearate, glycerine and propylene glycol. The monomeric plasticizer, if present, is preferably triethyl citrate and typically present in an amount of 0.1-4 wt.-%, preferably 0.5-1 wt.-%

Posaconazole has a melting point of 170-172° C., but it degrades at temperatures above 160° C. Hence, the hot-melt extrusion used for the preparation of the gastro-resistant pharmaceutical composition of the present invention has to be conducted at temperatures below 160° C. Preferably, the hot-melt extrusion is conducted at a temperature of 40-160° C., more preferred at a temperature of 120-150° C. and most preferred at a maximum temperature of 140° C. The hot-melt extrusion has to be carried out at a temperature that allows the dissolution of the posaconazole used as staring material within the mixture of the enteric polymer and optionally the non-enteric polymer. In principle, any crystalline form of posaconazole as well as the amorphous form may be used for the preparation of the gastro-resistant high-strength unit dosage form of the present invention.

The temperature of the hot-melt extrusion can be decreased when using a mixture of an enteric polymer and a non-enteric polymer, so that it is possible to process polymers with relatively high glass transitions temperatures. In addition, the non-enteric polymer, in particular polyvinylpyrrolidone, poly(vinylpyrrolidone/vinylacetate) and polyvinylcaprolactam/polyvinylacetate/polyethylene glycol graft copolymer, may serve as a solubility enhancer for posaconazole and may avoid recrystallization of the drug during dissolution in the intestines. Moreover, since the hot-melt extrusion works at relatively low temperatures, it is possible to use relatively volatile antioxidants as BHA and BHT as well as antioxidants, which degrade at processing temperatures above 140° C., e.g. sodium metabisulfite.

Typically, the weight ratio of the enteric polymer to posaconazole is in the range of 3.3:1 to 1.5:1, preferably it is 3.1:1 to 1.6:1, more preferred it is 2.8:1 to 1.8:1, even more preferred it is 2.73:1 to 2.0:1 and finally most preferred it is 2.3:1 to 2.0:1. The extrudate of the present invention may contain a non-enteric polymer and then, typically, the extrudate may contain the enteric polymer and the non-enteric polymer in a weight ratio of 10:1 to 3:1, preferably of 9:1 to 4:1, more preferred of 8:1 to 5:1 and most preferred of 7:1 to 6:1. Typically, the unit dosage form of the present invention may contain the enteric polymer, the optional non-enteric polymer and posaconazole in a weight ratio of enteric polymer to non-enteric polymer to posaconazole of 1.5-3.3:0-1:1 (enteric polymer:non-enteric polymer:posaconazole), preferably of 1.6-3.1:0.1-0.7:1, more preferred of 1.8-2.8:0.1-0.6:1 and most preferred of 2.0-2.7:0.3-0.5:1. According to a preferred embodiment of the present invention the enteric polymer is a mixture of poly(methacrylic acid/ethyl acrylate) and HPMCAS, and the non-enteric polymer is selected from poly(vinyl-pyrrolidone/vinylacetate), polyethylene glycol, hydroxypropyl cellulose and polyvinylpyrrolidone, most preferred hydroxypropyl cellulose.

It has been found that the presence of a sugar alcohol in the mixture that is subjected to hot-melt extrusion may increase the chemical stability of posaconazole and also the processability, in particular, if an acidic polymer as poly (methacrylic acid/ethyl acrylate) and HPMCAS, is present. Preferred sugar alcohols are xylitol, sorbitol, mannitol, maltitol, isomalt, lactitol and erythritol. The sugar alcohol, if present, is preferably xylitol and typically present in an amount of 0.5-9 wt.-%, preferably 2-6 wt.-%

The unit dosage form of the present invention is preferably prepared from a granulate material, whereby the granules may be coated with an enteric polymer. It is preferred that the enteric coating of the granules and the enteric polymer constituent of the granules comprise the same enteric polymer. According to a preferred embodiment of the present invention, the granules consist of posaconazole, an enteric polymer, a monomeric plasticizer, a sugar alcohol, and optionally an antioxidant and a non-enteric polymer. In such an embodiment the granules comprise 15.0-35.0 wt.-% of posaconazole, 35.0-75.0 wt.-% of enteric polymer, 0.1-5.0 wt.-% of a monomeric plasticizer, 0.5-9.0 wt.-% of a sugar alcohol and optionally 0.001-2.0 wt.-% of an antioxidant and 1.0-12.0 wt.-% of a non-enteric polymer: preferably 22.0-31.0 wt.-% of posaconazole, 55.0-71.0 wt.-% of enteric polymer, 0.6-4.0 wt.-% of a monomeric plasticizer, 2-6 wt.-% of a sugar alcohol and optionally 0.01-1.0 wt.-% of an antioxidant and 1.9-8.0 wt.-% of a non-enteric polymer; and most preferred 25.0-29.0 wt.-% of posaconazole, 67.0-71.0 wt.-% of enteric polymer, 0.7-1.0 wt.-% of a monomeric plasticizer, 2.2-3.0 wt.-% of a sugar alcohol and optionally about 0.25 wt.-% of an antioxidant and about 2 wt.-% of a non-enteric polymer.

The granules may be filled into a capsule or compressed into a tablet. The tablet, which is prepared by compressing the optionally enteric-coated granules of the present invention, may be coated with a film-coating in order to make swallowing of the tablet easier. Suitable film-coating systems are commercially available under the tradename Opadry®, e.g. Opadry® EZ.

In a preferred embodiment, the optionally film-coated tablet is prepared from granules containing posaconazole molecularly dispersed in a mixture containing poly(methacrylic acid/ethyl acrylate), triethyl citrate, hydroxypropyl methylcellulose acetate succinate, xylitol, propyl gallate and optionally hydroxypropyl cellulose.

The capsule or tablet of the present invention may contain additional pharmaceutical excipients as extragranular component, e.g. diluents, binders, disintegrants, glidants and lubricants. Examples of diluents include microcrystalline cellulose, calcium hydrogen phosphate, lactose (anhydrous or monohydrate), and calcium carbonate. As binders may be used methyl cellulose, hydroxypropyl methylcellulose (HPMC), hydroxypropyl cellulose (HPC), pregelatinized starch, povidone and copovidone. Examples of disintegrants include croscarmellose sodium, sodium starch glycolate, polyvinylpolypyrrolidone (crospovidone) and low-substituted hydroxypropyl cellulose (L-HPC). As glidants silicone dioxide, talk and the like may be used, while magnesium stearate, calcium stearate, stearic acid, sodium stearyl fumarate and glycerol dibehenate are examples of suitable lubricants.

In case the granules of the present invention are filled into a capsule, the capsule has size 0 or 00. In a preferred embodiment, the granules of the present invention are compressed into a tablet. The tablet has a weight of 1200 mg to 1650 mg. Preferably the weight of the tablet is 1300 mg to 1550 mg, more preferred 1390 mg to 1480 mg and most preferred 1390 mg or 1450 mg; the weight relates to the tablet core if the tablet is film-coated. The tablet may contain a break-line.

The following examples are intended to further illustrate the present invention.

EXAMPLES

Hot melt extrusion was performed with a Pharma 11 Twin-screw hot melt extruder from Thermo Fisher Scientific Inc. The used film coating system Opadry® II 85F520152 yellow comprises polyvinyl alcohol, titanium dioxide, polyethylene glycol/macrogol, talc and yellow iron oxide, and Opadry® EZ comprises maltodextrin, talc, hydroxypropyl methylcellulose, guar gum, and medium chain triglycerides The dissolution tests were performed according to the general dissolution test of Monograph '2.9.3 Dissolution test for solid dosage forms' (for delayed-release solid dosage forms) of the European Pharmacopeia 8.0 with the following conditions: USP apparatus II (paddle); speed: 75 rpm; acid stage: 750 ml of 0.01 N HCl for 2 h, followed by buffer stage: 50 mM phosphate buffer (pH 6.8) containing 1.095% (1.1%) polysorbate 80 (1000 ml); time points: acid stage: 120 min; time points buffer stage: 5, 10, 15, optionally 20, 30 and 45 (and/or 60) min; samples: 6 units.

Example 1

| Ingredients | Ex. 1a mg | Ex. 1b mg | % w/w |
|---|---|---|---|
| Stage-A: (Granulation) | | | |
| Methacrylic Acid/Ethyl Acrylate Copolymer (1:1), Type B (Kollicoat MAE 100P) | 300 | 300 | 22.06 |
| Triethyl Citrate (Citrifol AI) | 10 | 10 | 0.74 |
| Weight of Granules | 310 | 310 | |
| Stage-B: (Hot-melt extrusion) | | | |
| Posaconazole (Form-1) | 300 | 300 | 22.11 |
| Xylitol (Xylisorb 90) | 60 | 60 | 4.41 |
| Hypromellose Acetate Succinate (Aqoat AS-MG) | 375 | 375 | 27.57 |
| Propyl Gallate | 3 | 3 | 0.22 |
| Weight of HME Granules | 1048 | 1048 | |
| Stage-C: (Lubrication) | | | |
| Microcrystalline Cellulose (Comprecel M 102D+) | 121 | 121 | 8.84 |
| Hydroxypropylcellulose (Klucel EXF) | 100 | 100 | 7.35 |
| Colloidal Anhydrous Silica (Aerosil 200) | 10 | 10 | 0.74 |
| Croscarmellose Sodium (Ac-Di-Sol) | 75 | 75 | 5.51 |
| Sodium Stearyl Fumarate (Pruv) | 6 | 6 | 0.44 |
| Core tablet weight | 1360 | 1360 | |
| Stage-D: (Film Coating) | | | |
| Opadry ® II Yellow 85F520152 | 40 | 40 | — |
| Water, Purified | q.s. | q.s. | — |
| Stage-E: (Clear Film Coating) | | | |
| Opadry ® EZ Clear 253U190007 | 14 | 21 | — |
| Water, Purified | q.s. | q.s. | — |
| Film-coated tablet weight | 1414 | 1421 | |

Process:

The excipients of stage A were sifted and granulated. Posaconazole and the excipients of stage B were sifted and blended with the granules of stage A. The mixture was subjected to hot-melt extrusion and the obtained extrudate was milled. Microcrystalline cellulose, hydroxypropyl cellulose, silicon dioxide, croscarmellose sodium and sodium stearyl fumarate were sifted and blended with the milled extrudate and then subjected to compression to obtain a tablet, which was finally film-coated successively with Opadry® II Yellow and Opadry® EZ Clear.

| Parameters of the core tablets | Ex. 1b |
|---|---|
| Tablet weight (mg) | 1354-1365 |
| Thickness (mm) | 7.40-7.50 |
| Hardness (N) | 193-218 |
| Disintegration time (min) | 5'50"-7'56" |

| | Dissolution / Drug Release [%] in 0.01N HCl for 2 h followed by pH 6.8 phosphate buffer |
|---|---|
| Time [min] | Ex. 1b |
| Acid stage | |
| 120 | 4 |
| Buffer stage | |
| 5 | 68 |
| 10 | 89 |
| 15 | 97 |
| 30 | 100 |
| 60 | 100 |

Example 2

| Ingredients | mg | % w/w |
|---|---|---|
| Stage-A: (Granulation) | | |
| Methacrylic Acid/Ethyl Acrylate Copolymer (1:1), Type B (Kollicoat MAE 100P) | 300 | 22.06 |
| Triethyl Citrate (Citrifol AI) | 40 | 2.94 |
| Weight of Granules | 340 | |
| Stage-B: (Hot-melt extrusion) | | |
| Posaconazole (Form-1) | 300 | 22.06 |
| Xylitol (Xylisorb 90) | 30 | 2.21 |
| Hypromellose Acetate Succinate (Aqoat AS-MF) | 300 | 22.06 |
| Hydroxypropylcellulose (Klucel EXF) | 75 | 5.51 |
| Propyl Gallate | 3 | 0.22 |
| Weight of HME Granules | 1048 | |
| Stage-C: (Lubrication) | | |
| Microcrystalline Cellulose (Comprecel M 102D+) | 146 | 10.74 |
| Hydroxypropylcellulose (Klucel EXF) | 75 | 5.51 |
| Colloidal Anhydrous Silica (Aerosil 200) | 10 | 0.74 |
| Croscarmellose Sodium (Ac-Di-Sol) | 75 | 5.51 |
| Sodium Stearyl Fumarate (Pruv) | 6 | 0.44 |
| Core tablet weight | 1360 | |
| Stage-D: (Film Coating) | | |
| Opadry ® II Yellow 85F520152 | 40 | — |
| Water, Purified | q.s. | — |
| Film-coated tablet weight | 1400 | |

Process:

The tablet was prepared as in Example 1.

| Parameters of the core tablets | |
|---|---|
| Tablet weight (mg) | 1359-1370 |
| Thickness (mm) | 7.52-7.57 |
| Hardness (N) | 233-254 |
| Disintegration time (min) | 24'05"-28'25" |
| Parameters of the film-coated tablets | |
| Description | Approximately 21.3 × 10.4 mm, Yellow coated, capsule shaped tablets plain on both the sides |
| Tablet weight (mg) | 1399-1404 |
| Thickness (mm) | 7.78-7.82 |
| Hardness (N) | 267-284 |
| Disintegration time (min) | 26'29"-29'55" |

| Time [min] | Dissolution / Drug Release [%] in 0.01N HCl for 2 h followed by pH 6.8 phosphate buffer |
| --- | --- |
| Acid stage | |
| 120 | 6 |
| Buffer stage | |
| 5 | 58 |
| 10 | 81 |
| 15 | 90 |
| 30 | 96 |
| 60 | 95 |

Example 3

| Ingredients | Ex. 3a | | Ex. 3b | |
| --- | --- | --- | --- | --- |
| | mg | % w/w | mg | % w/w |
| Stage-A: (Granulation) | | | | |
| Methacrylic Acid/Ethyl Acrylate Copolymer (1:1), Type B (Kollicoat MAE 100P) | 450 | 30.97 | 450 | 32.37 |
| Triethyl Citrate (Citrifol AI) | 10 | 0.69 | 10 | 0.72 |
| Weight of Granules | 460 | | 460 | |
| Stage-B: (Hot-melt extrusion) | | | | |
| Posaconazole (Form-1) | 300 | 20.65 | 300 | 21.58 |
| Xylitol (Xylisorb 90) | 30 | 2.06 | 60 | 4.32 |
| Hypromellose Acetate Succinate (Aqoat AS-MMP) | 369 | 25.40 | 200 | 14.39 |
| Hydroxypropylcellulose (Klucel EXF) | 25 | 1.72 | 50 | 3.60 |
| Propyl Gallate | 3 | 0.21 | 3 | 0.21 |
| Weight of HME Granules | 1187 | | 1073 | |
| Stage-C: (Lubrication) | | | | |
| Microcrystalline Cellulose (Comprecel M 102D+) | 100 | 6.88 | 151 | 10.86 |
| Hydroxypropylcellulose (Klucel EXF) | 75 | 5.16 | 75 | 5.40 |
| Colloidal Anhydrous Silica (Aerosil 200) | 10 | 0.69 | 10 | 0.72 |
| Croscarmellose Sodium (Ac-Di-Sol) | 75 | 5.16 | 75 | 5.40 |
| Sodium Stearyl Fumarate (Pruv) | 6 | 0.41 | 6 | 0.43 |
| Core tablet weight | 1453 | | 1390 | |
| Stage-D: (Film Coating) | | | | |
| Opadry ® II Yellow 85F520152 | 47 | — | 46 | — |
| Water, Purified | q.s. | — | q.s. | — |
| Film-coated tablet weight | 1500 | | 1436 | |
| Stage-E: (Clear Film Coating) | | | | |
| Opadry EZ ® Clear 253U190007 | — | — | 14 | — |
| Water, Purified | — | — | q.s. | — |
| Final Film-Coated tablet weight | — | | 1450 | |

Process:

The excipients of stage A were sifted and granulated. Posaconazole and the excipients of stage B were sifted and blended with the granules of stage A. The mixture was subjected to hot-melt extrusion and the obtained extrudate was milled. Microcrystalline cellulose, hydroxypropyl cellulose, silicon dioxide, croscarmellose sodium and sodium stearyl fumarate were sifted and blended with the milled extrudate and then subjected to compression to obtain a tablet, which was finally film-coated successively with Opadry® II Yellow and Opadry® EZ Clear (only example 3b).

| | Ex. 3a | Ex. 3b |
| --- | --- | --- |
| Parameters of the core tablets | | |
| Tablet weight (mg) | 1445-1460 | 1389-1399 |
| Thickness (mm) | 7.92-7.99 | 7.82-7.88 |
| Hardness (N) | 198-210 | 209-230 |
| Disintegration time (min) | 1'45"-3'30" | 8 min 20 sec |
| Parameters of the film-coated tablets | | |
| Description | Approximately 22.5 × 11 mm, yellow coated, oval shaped tablets, notched on either side, break line on one side and plain on other side. | 22 × 11 mm yellow coated, oval shaped, biconvex tablets, notched on either side along with the break line on one side and debossed with "P300" on the other side. |
| Tablet weight (mg) | 1502-1512 | 1442-1459 |
| Thickness (mm) | 8.15-8.29 | 7.99-8.06 |
| Hardness (N) | 246-288 | 270-290 |
| Disintegration time (min) | 3'29"-4'48" | 8 min 40 sec |

| Time [min] | Dissolution / Drug Release [%] in 0.01N HCl for 2 h followed by pH 6.8 phosphate buffer | |
| --- | --- | --- |
| | Ex. 3a | Ex. 3b |
| Acid stage | | |
| 120 | 3 | 4 |
| Buffer stage | | |
| 5 | 52 | 61 |
| 10 | 75 | 86 |
| 15 | 87 | 95 |
| 20 | 93 | 97 |
| 30 | 98 | 98 |
| 45 | 99 | 98 |
| 60 | 99 | |

Example 4

| Ingredients | Ex. 4a | | Ex. 4b | |
| --- | --- | --- | --- | --- |
| | mg | % w/w | mg | % w/w |
| Stage-A: (Granulation) | | | | |
| Methacrylic Acid/Ethyl Acrylate Copolymer (1:1), Type B (Kollicoat MAE 100P) | 450 | 32.37 | — | — |
| Methacrylic Acid-Ethyl Acrylate Copolymer (1:1), Type A (Eudragit L100-55) | — | — | 450 | 32.37 |
| Triethyl Citrate (Citrifol AI) | 10 | 0.72 | 10 | 0.72 |
| Stage-B: (Hot-melt extrusion) | | | | |
| Posaconazole (Form-1) | 300 | 21.58 | 300 | 21.58 |
| Xylitol (Xylisorb 90) | 60 | 4.31 | 60 | 4.31 |
| Hypromellose Acetate Succinate (Aqoat AS-MG) | — | — | 200 | 14.39 |
| Methacrylic Acid-Ethyl Acrylate Copolymer (1:1), Type A (Eudragit L100-55) | 200 | 14.39 | — | — |
| Hydroxypropylcellulose (Klucel EXF) | 50 | 3.60 | 50 | 3.60 |
| Propyl Gallate | 3 | 0.22 | 3 | 0.22 |
| Weight of HME Granules | 1073 | | 1073 | |
| Stage-C: (Lubrication) | | | | |
| Microcrystalline Cellulose (Comprecel M 102D+) | 151 | 10.86 | 151 | 10.86 |
| Hydroxypropylcellulose (Klucel EXF) | 75 | 5.40 | 75 | 5.40 |
| Colloidal Anhydrous Silica (Aerosil 200) | 10 | 0.72 | 10 | 0.72 |

-continued

| Ingredients | Ex. 4a | | Ex. 4b | |
|---|---|---|---|---|
| | mg | % w/w | mg | % w/w |
| Croscarmellose Sodium (Ac-Di-Sol) | 75 | 5.40 | 75 | 5.40 |
| Sodium Stearyl Fumarate (Pruv) | 6 | 0.43 | 6 | 0.43 |
| Core tablet weight | 1390 | | 1390 | |
| Stage-D: (Film Coating) | | | | |
| Opadry ® II Yellow 85F520152 | 46 | — | 46 | — |
| Water, Purified | q.s. | — | q.s. | — |
| Stage-E: (Clear Film Coating) | | | | |
| Opadry ® EZ Clear 253U190007 | 14 | — | 14 | — |
| Water, Purified | q.s. | — | q.s. | — |
| Film-coated tablet weight | 1450 | | 1450 | |

Process:

The excipients of stage A were sifted and granulated. Posaconazole and the excipients of stage B were sifted and mixed with the granules of stage A (in RMG). The mixture was subjected to hot-melt extrusion and the obtained extrudate was milled. Microcrystalline cellulose, hydroxypropyl cellulose, silicon dioxide, croscarmellose sodium and sodium stearyl fumarate were sifted and blended with the milled extrudate and then subjected to compression to obtain a tablet, which was finally film-coated successively with Opadry® II Yellow and Opadry® EZ Clear.

| | Ex. 4a | Ex. 4b |
|---|---|---|
| Parameters of the core tablets | | |
| Tablet weight (mg) | 1391-1400 | 1392-1398 |
| Thickness (mm) | 7.99-8.02 | 7.85-7.89 |
| Hardness (N) | 212-232 | 216-237 |
| Disintegration time (min) | 4 min 20 sec | 2 min 25 sec |
| Parameters of the film-coated tablets | | |
| Description | 22 × 11 mm yellow coated, oval shaped, biconvex tablets, notched on either side along with the break line on one side and debossed with "P300" on the other side. | |
| Tablet weight (mg) | 1446-1457 | 1455-1477 |
| Thickness (mm) | 8.18-8.21 | 8.08-8.15 |
| Hardness (N) | 266-290 | 290-321 |
| Disintegration time (min) | 6 min 20 sec | 4 min 45 sec |

| | Dissolution / Drug Release [%] in 0.01N HCl for 2 h followed by pH 6.8 phosphate buffer | |
|---|---|---|
| Time [min] | Ex. 4a | Ex. 4b |
| Acid stage | | |
| 120 | 4 | 6 |
| Buffer stage | | |
| 5 | 70 | 78 |
| 10 | 89 | 92 |
| 15 | 97 | 97 |
| 20 | 98 | 99 |
| 30 | 99 | 98 |
| 45 | 99 | 99 |

The invention claimed is:

1. A gastro-resistant unit dosage form, which is an optionally film-coated tablet, containing 300 mg posaconazole, wherein posaconazole is molecularly dispersed in a mixture comprising an enteric polymer and optionally a non-enteric polymer, wherein the weight ratio of the enteric polymer to posaconazole is in the range of 3.3:1 to 1.5:1, wherein the tablet core has a weight of 1200 mg to 1650 mg, and wherein the enteric polymer is a mixture of poly(methacrylic acid/ethyl acrylate) and hydroxypropyl methylcellulose acetate succinate.

2. The unit dosage form according to claim 1, wherein the mixture is prepared by hot-melt extrusion.

3. The unit dosage form according to claim 1, wherein the non-enteric polymer is selected from the group consisting of polyvinylpyrrolidone, poly(vinyl-pyrro-lidone/vinylacetate), polyvinylcaprolactam/polyvinylacetate/polyethylene glycol graft copolymer, polyethylene glycol/polyvinyl alcohol graft copolymer, polyethylene oxide, polypropylene oxide, copolymers of ethylene oxide and propylene oxide, polyacrylates, polymethacrylates, copolymers of vinyl acetate and crotonic acid, polyvinyl alcohol, partially saponified polyvinylalcohol, macrogolglycerol hydroxystearate, polyethylene glycol, hypromellose, hydroxypropyl cellulose, hydroxy ethyl cellulose and maltodextrins.

4. The unit dosage form according to claim 3, wherein the non-enteric polymer is selected from the group consisting of poly(vinyl-pyrrolidone/vinylacetate), polyethylene glycol, hydroxypropyl cellulose and polyvinylpyrrolidone.

5. The unit dosage form according to claim 1, wherein the unit dosage form contains an antioxidant.

6. The unit dosage form according to claim 5, wherein the antioxidant is selected from the group consisting of butylated hydroxytoluene (BHT), butylated hydroxyanisole (BHA), sodium or potassium metabisulfite, sodium bisulfite, sodium sulfite, sodium thio-sulfate, cysteine, acetyl cysteine, methionine, glutathione, sodium formaldehyde sulfoxylate, ascorbic acid and its derivatives, ascorbyl palmitate, tocopherol and its derivatives, tocopheryl succinate, tocopheryl polyethylene glycol succinate (TPGS) and propyl gallate.

7. The unit dosage form according to claim 1, wherein the mixture contains a monomeric plasticizer.

8. The unit dosage form according to claim 7, wherein the monomeric plasticizer is selected from the group consisting of triethyl citrate, triacetin, dibutyl sebacate, diethyl phthalate, glycerylmonostearate, glycerine and propylene glycol.

9. The unit dosage form according to claim 1, wherein the mixture contains a sugar alcohol.

10. The unit dosage form according to claim 9, wherein the sugar alcohol is selected from the group consisting of xylitol, sorbitol, mannitol and maltitol.

11. The unit dosage form according to claim 1, wherein the unit dosage form is prepared from a granulate material.

12. The unit dosage form according to claim 11, wherein the granulate material is compressed into an optionally film-coated tablet.

13. The unit dosage form according to claim 12, which is an optionally film-coated tablet, wherein posaconazole is molecularly dispersed in a mixture containing poly(methacrylic acid/ethyl acrylate), triethyl citrate, hydroxypropyl methylcellulose acetate succinate, xylitol, propyl gallate and optionally hydroxypropyl cellulose.

14. The unit dosage form according to claim 5, wherein the antioxidant is contained in the mixture.

* * * * *